United States Patent [19]

Falciani et al.

[11] 4,380,630
[45] Apr. 19, 1983

[54] N-CARBOXY CEFADROXIL SODIUM SALT

[75] Inventors: Marco Falciani; Renato Broggi, both of Milan, Italy

[73] Assignee: Dobfar S.p.A., Milan, Italy

[21] Appl. No.: 240,311

[22] Filed: Mar. 4, 1981

[30] Foreign Application Priority Data

Apr. 1, 1980 [IT] Italy ................................ 21096 A/80

[51] Int. Cl.³ .......................................... C07D 501/22
[52] U.S. Cl. ...................................................... 544/30
[58] Field of Search ............................................ 544/30

[56] References Cited
U.S. PATENT DOCUMENTS 3,489,752  1/1970  Grast ..................................... 544/30
3,741,963  6/1973  Dursch et al. ......................... 544/30
3,985,741 10/1976  Crast et al. ............................ 544/30
4,016,158  4/1977  Martel et al. .......................... 544/30

Primary Examiner—Paul M. Coughlan, Jr.
Attorney, Agent, or Firm—Oblon, Fisher, Spivak, McClelland & Maier

[57] ABSTRACT

N-carboxy cefadroxil disodium salt having formula

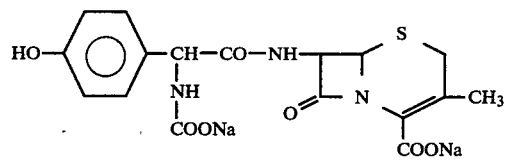

Said salt is endowed with antibiotic activity and can be administered parenterally.

1 Claim, No Drawings

N-CARBOXY CEFADROXIL SODIUM SALT

BACKGROUND OF THE INVENTION

1. Field of the Invention

The present invention relates to the N-carboxy cefadroxil disodium salt.

2. Description of the Prior Art

Cefadroxil is a well known antibiotic, which is described in U.S. Pat. No. 3,985,741: it is a broad spectrum antibiotic which is administered orally.

DETAILED DESCRIPTION OF THE INVENTION

Object of the present invention is to provide a cefadroxil derivative which can be administered parenterally and which maintains unaltered the antibiotic characteristics of parent compound.

Said object is attained by means of a cefadroxil derivative having the formula

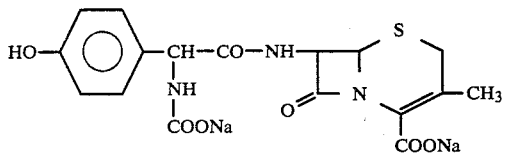

Compounds having similar structure are described in Dutch Patent Application No. 7210416: these compounds consist of N-carboxy cephalexin and N-carboxy cephradine disodium salts.

The compound according to the present invention is the N-carboxy cefadroxil disodium salt, which is different from previously cited compounds in the aromatic ring substitution.

In order that this invention may be readily available to and understood by those skilled in the art, the following methods of preparing the salt, which is object of the present invention, are described.

EXAMPLE 1

N-carboxy cefadroxil disodium salt

To a suspension of cefadroxil monohydrate (38.1 g, 0.1 mole) in water (110 ml) at 15° C. was added portionwise sodium carbonate (10.6 g, 0.1 mole).

After stirring for 0.5 hours at 15°–20° C., acetone (280 ml) was added in 15 minutes. After stirring for 2 hours, a white crystalline material was obtained. After cooling at 0° C. and further dilution with acetone (250 ml), the solution was allowed to crystallize for 24 hours. Precipitate was separated by filtration, was washed with acetone (50 ml) and submitted to vacuum drying at 40° C.

26 g of N-carboxy cefadroxil disodium salt were obtained

Water content: 7.5%
Sodium carbonate: 13.6%
N-carboxy cefadroxil: 78.9%
$[\alpha]_D$ (C=1, $H_2O$) = +147° (on the dry base)
$E_1^{1\%}{}_{cm}$ at 262 nm = 196
Microbiological titer = 789 mcg/mg as cefadroxil

EXAMPLE 2

N-carboxy cefadroxil disodium salt

To a suspension of cefadroxil dimethylformamide solvate (43.6 g, 0.1 mole) in water (110 ml) was added portionwise sodium carbonate (10.6 g, 0.1 mole).

After stirring for 0.5 hours at 10°–15° C., acetone (300 ml) was added in 20 minutes. After stirring for 1.5 hours, a white crystalline material crystallized.

After cooling at 0° C. and further dilution with acetone (250 ml), the solution was allowed to crystallize for 2 hours. Precipitate was separated by filtration, was washed with acetone (50 ml) and submitted to vacuum drying at 40° C.

27.5 g of N-carboxy cefadroxil disodium salt were obtained.

Water content: 7.8%
Sodium carbonate: 13.4%
N-carboxycefadroxil: 78.8%
$[\alpha]_D$ (c=1, $H_2O$) = +145° (on the dry base)
$E_1^{1\%}{}_{cm}$ at 262 nm = 193
Microbiological titer = 788 mcg/mg as cefadroxil

What is claimed is:

1. The N-carboxy cefadroxil disodium salt having formula

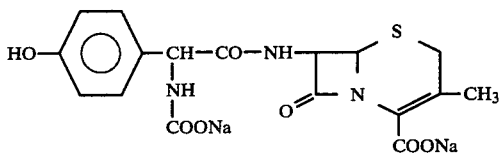

* * * * *